(12) United States Patent
Bellikli et al.

(10) Patent No.: US 10,856,949 B2
(45) Date of Patent: Dec. 8, 2020

(54) STERILE CONTAINER COMPRISING A GAS-PERMEABLE FILTER CASSETTE

(71) Applicant: Aesculap AG, Tuttlingen (DE)

(72) Inventors: Serkan Bellikli, Schömberg (DE); John Gray-Dreizler, Rottweil (DE); Andreas Elisch, Schramberg (DE); Josef-Benedikt Weiss, Rottweil (DE)

(73) Assignee: AESCULAP AG, Tuttlingen (DE)

( * ) Notice: Subject to any disclaimer, the term of this patent is extended or adjusted under 35 U.S.C. 154(b) by 193 days.

(21) Appl. No.: 16/079,731

(22) PCT Filed: Feb. 21, 2017

(86) PCT No.: PCT/EP2017/053913
§ 371 (c)(1),
(2) Date: Aug. 24, 2018

(87) PCT Pub. No.: WO2017/144453
PCT Pub. Date: Aug. 31, 2017

(65) Prior Publication Data
US 2019/0046285 A1    Feb. 14, 2019

(30) Foreign Application Priority Data

Feb. 25, 2016   (DE) .................. 10 2016 103 342

(51) Int. Cl.
*A61B 50/30*       (2016.01)
*A61L 2/07*        (2006.01)
(Continued)

(52) U.S. Cl.
CPC ............... *A61B 50/30* (2016.02); *A61L 2/07* (2013.01); *A61L 2/26* (2013.01); *B01D 46/0002* (2013.01);
(Continued)

(58) Field of Classification Search
CPC ............... B01D 46/00; B01D 46/0002; B01D 46/0004; B01D 46/0005; B01D 46/0006;
(Continued)

(56) References Cited

U.S. PATENT DOCUMENTS 4,562,047 A   12/1985   Sestak et al.
6,620,390 B1   9/2003   Wagner
(Continued)

FOREIGN PATENT DOCUMENTS

DE   88114071 U1   1/1989
DE   19753671 A1   6/1999
(Continued)

OTHER PUBLICATIONS

International Search Report and Written Opinion for International Application No. PCT/EP2017/053913, dated Sep. 6, 2017—7 pages.
(Continued)

*Primary Examiner* — Jason M Greene

(57) ABSTRACT

A filter cassette which is part of a filter system can be fastened to a sterile container lid. The sterile container lid serves to close a sterile container and to make a gas exchange possible between the container exterior and the container interior, without recontaminating the container material. In addition, the filter system fulfils a valve function. In order to center the filter cassette with respect to the sterile container lid, a first centering portion is provided on the filter cassette. The first centering portion interacts with a second centering portion on the sterile container wall section when the filter cassette is inserted into the sterile container lid.

21 Claims, 3 Drawing Sheets

(51) Int. Cl.
  *A61L 2/26* (2006.01)
  *B01D 46/00* (2006.01)
  *A61B 50/00* (2016.01)

(52) U.S. Cl.
  CPC ..... *B01D 46/0004* (2013.01); *B01D 46/0006* (2013.01); *A61B 2050/005* (2016.02); *A61B 2050/006* (2016.02); *A61L 2202/182* (2013.01)

(58) Field of Classification Search
  CPC ........ A61L 2/07; A61L 2/26; A61L 2202/182; A61B 50/30; A61B 2050/005; A61B 2050/006
  See application file for complete search history.

(56) References Cited

U.S. PATENT DOCUMENTS

| | | |
|---|---|---|
| 7,172,740 B2 | 2/2007 | Gleichauf et al. |
| 7,381,385 B2 | 6/2008 | Gleichauf et al. |
| 2004/0256269 A1* | 12/2004 | Gleichauf ................ A61L 2/26 206/439 |
| 2005/0045551 A1* | 3/2005 | Jakab ........................ A61L 2/26 210/436 |
| 2009/0223187 A1* | 9/2009 | Nelson ............... B01D 46/0005 55/357 |
| 2012/0189508 A1 | 7/2012 | Kreidler |
| 2014/0318091 A1* | 10/2014 | Rieger ............... B01D 46/0005 46/5 |

FOREIGN PATENT DOCUMENTS

| | | | |
|---|---|---|---|
| DE | 20203984 | U1 | 6/2002 |
| DE | 102004020805 | B3 | 1/2006 |
| DE | 202011001772 | U1 | 4/2011 |
| DE | 102012102167 | A1 | 11/2011 |
| GB | 908407 | * | 10/1962 |
| WO | 03041604 | A1 | 5/2003 |

OTHER PUBLICATIONS

German Search Report for Application No. 10 2016 103 342.1, dated Oct. 19, 2016, 2013—11 pages.

* cited by examiner

STERILE CONTAINER COMPRISING A GAS-PERMEABLE FILTER CASSETTE

CROSS REFERENCE TO RELATED APPLICATIONS

This application is the United States national phase entry of International Application No. PCT/EP2017/053913, filed Feb. 21, 2017, which claims the benefit of priority of German Application No. 10 2016 103 342.1, filed Feb. 25, 2016. The contents of International Application No. PCT/EP2017/053913 and German Application No. 10 2016 103 342.1 are incorporated by reference herein in their entireties.

FIELD

The present disclosure relates to a sterile container with a gas-permeable filter cassette.

BACKGROUND

In the vast majority of clinical procedures and operations, it is essential to ensure the sterility of the instruments and/or other aids used. For this reason, sterile containers or cases (also referred to as sterilization containers or cases) are used, which are loaded/filled with medical instruments, for example. The sterile container in the loaded state is then heated for instance in an autoclave for a predetermined period of time to a predetermined sterilization temperature until any microorganisms adhering to the medical instruments have been killed.

In this process, a sterile filter is required to prevent germs from entering the receiving space of the sterile container after the sterilization process. Since the gas flow rate is limited by a sterile filter, a pressure relief valve may be additionally provided in the sterile container to compensate for a large pressure difference between the container exterior and the container interior and to prevent damage to the sterile container. Such a large pressure difference occurs, for example, during sterilization of the material inside the container by means of saturated water vapor. From prior art, various embodiments of filter cassettes and sterile containers with such filter cassettes are already known which, on the one hand, protect the contents of the sterile container from contamination by germs after sterilization and, on the other hand, open a further flow path in the event of a high pressure difference between the container exterior and the container interior.

For example, a sterile container is known from DE 88 14 071 U1, in which a flow path bypassing a sterile filter is opened when a predetermined pressure difference is exceeded. In the initial position, a cover plate and a filter plate are pressed away from a cover by coil springs and a gas exchange between the environment and the receiving space is only possible through the filter plate. When the predetermined pressure difference is exceeded, the cover plate and the filter plate are displaced toward the cover and protected against the entering gas by several silicone seals, which gas uses a flow path opened due to the displacement to penetrate into the receiving space. The cover plate and the filter plate are centered via a bearing pin and must be additionally sealed accordingly. The configuration disclosed in DE 88 14 071 U1 thus consists of many individual parts, which make it difficult to assemble, handle and replace the filter system in several steps and increase the overall weight of the design. In addition, several seals are required to ensure a sterile barrier and the cover plate makes it impossible to check the condition of the filter material from all sides.

Moreover, DE 202 03 984 U1 reveals a sterile container with a filter unit consisting of a holding frame, a filter element and a cover. The parts are made of plastic, which leads to problems during drying. For assembly, the holding frame must be fastened to the sterile container and the filter element and the cover must be fastened to the holding frame. The sealing is achieved between the filter element and the sterile container, but the pressing force is generated by return springs between the sterile container and the holding frame. It is therefore difficult to ensure a secure sealing, as the contact force is not applied locally close to the seal.

Further sterile containers with filter systems are described in DE 10 2004 020 805 B3 and DE 197 53 671 A1.

SUMMARY

Against this background, the present disclosure is based on the object of developing a sterile barrier system that guarantees a reliable operation with a simple construction.

A gas-permeable filter cassette of the sterile container according to the disclosure comprises a filter element arranged in the filter cassette, wherein a first conical centering means is provided on the filter cassette for centering the filter cassette with regard to a sterile container wall section which has at least one gas exchange opening, which centering means cooperates in a non-self locking manner with a second centering means provided on the sterile container wall section when the filter cassette is (loosely) inserted in or arranged on the sterile container wall section. The first centering means and the second centering means may be located in the middle or centrally on the filter cassette and on the sterile container wall section.

At least one centering means can have a centrally tapering sliding or contact surface, which positions the filter cassette centrally to the gas exchange opening when returning from a deflected position to its contact position.

The first centering means may in particular be a conical projection or a conical seating in the filter cassette so that the filter cassette with a correspondingly complementary seating or a correspondingly complementary projection as the second centering means on the sterile container wall section forms a non-self locking conical seat when the filter cassette is inserted in or arranged on the sterile container wall section.

The centering, in particular the conical seat, allows the filter cassette to be inserted into the sterile container wall section without the risk of tilting or jamming, as is the case e.g. with a linear guide. This simplifies handling, as the correct position is quickly and easily found when inserting the filter cassette, especially with regard to the gas exchange opening in the sterile container wall section. Furthermore, due to the centering by means of a conical seat, no additional continuous recess or the like must be provided in the filter cassette, which would involve an additional and complex seal, for example. It is possible to realize the conical seat by means of a conical projection in the filter cassette and a complementary seating in the sterile container wall section, as well as to form the conical seat by a conical seating in the filter cassette and a complementary projection on the sterile container wall section.

According to one aspect of the disclosure, the filter cassette may consist of an upper clamping disc and a lower clamping disc.

According to one aspect of the disclosure, the filter element may be arranged between the upper clamping disc and the lower clamping disc.

This makes it easy to manufacture and assemble the filter cassette, as the individual components do not form complex shapes and can be pressed together in just one manufacturing step.

This means that the filter material, i.e. the filter element, is framed in a cassette by the upper clamping disc and the lower clamping disc, and the filter material can be protected from getting damaged.

According to one aspect of the disclosure, a sealing ring may be provided on the filter cassette.

According to one aspect of the disclosure, the sealing ring may be provided on the side of the filter cassette facing the sterile container wall section.

According to one aspect of the disclosure, the sealing ring may be located in an outer peripheral portion of the filter cassette.

The outer peripheral portion is an area which can be connected flush to the outer edge of the filter cassette or the lower clamping disc. In any case, it is dimensioned such that the sealing ring completely surrounds the gas exchange opening provided in the sterile container wall section. Thus, a sealing between the sterile container wall section and the filter cassette is realized by only one seal in the outer peripheral portion of the filter cassette.

According to one aspect of the disclosure, the upper clamping disc and the lower clamping disc may be realized in the shape of a spoke wheel.

In other words, the design of the upper clamping disc and the lower clamping disc can be based on the shape of diatoms. This bionic approach allows the weight and the installation space (especially the height) of the filter cassette to be optimized while maintaining the same mechanical properties.

A filter system of the sterile container according to the disclosure comprises a filter cassette, a spring and a cover which can be mounted on the sterile container wall section and in which the filter cassette is received so as to be axially movable against the preload force of the spring.

The cover is designed here in such a way that it has openings that enable a gas exchange. On the other hand, the openings are so small that they reliably protect the filter cassette located in the cover from damage, e.g. by objects received in the sterile container.

According to one aspect of the disclosure, the spring can be designed as a kind of leaf spring or disk spring.

This makes it possible to introduce the spring force near the sealing point into the system, more precisely into the filter cassette.

According to one aspect of the disclosure, the spring may be fastened to the cover.

According to one aspect of the disclosure, the spring may be fastened to the cover by means of a central pin.

This makes it possible to remove the spring together with the cover when dismantling the filter system, e.g. to check or replace the filter cassette. This means that there are no individual parts that can get lost during removal.

According to one aspect of the disclosure, the spring can be supported by the cover and the filter cassette.

According to one aspect of the disclosure, the spring can be supported in the middle of the cover and the filter cassette.

According to one aspect of the disclosure, the combined height of the unloaded spring and the filter cassette can be greater than the height of the cover.

In other words, when mounting the cover to the sterile container wall section, the spring must be compressed to reduce its height. This makes the combined height of the preloaded spring and the filter cassette less than or equal to the height of the cover, and the cover can be locked. Consequently, when the cover is mounted, a preload force of the spring acts on the filter cassette toward the sterile container wall section. This ensures, on the one hand, that the filter cassette including the seal is securely pressed down and, on the other hand, the spring force is supported centrally (in the middle of the cover). This also ensures that the filter cassette is kept closed securely.

According to one aspect of the disclosure, the cover may have the shape of a spoke heel.

According to one aspect of the disclosure, the cover may be made of aluminum.

The force absorption requires that the cover is designed to be very rigid. On the other hand, there is the requirement that the filter system must be very light-weight so that the maximum loading of the container with sterile goods is restricted as little as possible. The bionic approach according to which the design of the cover is based on the shape of diatoms, discloses an innovative lightweight structure which allows to reduce the weight while maintaining the same mechanical properties. In addition, the use of aluminum offers advantages in drying by reducing the proportion of plastic.

Furthermore, it is advantageous that due to the relatively low weight of the filter cassette and the operating principle of the selected concept, the filter system has a comparably small movable inertial mass and thus the safety during transport is increased. In other words, due to the small mass, the acceleration acting on the filter cartridge is low, making it unlikely that the filter cartridge will move against the preload force of the spring.

A sterile container lid of the sterile container according to the disclosure comprises a filter system according to the disclosure.

According to one aspect of the disclosure, the cover can be locked to the sterile container lid.

According to one aspect of the disclosure, the cover can be locked to the sterile container lid by means of a bayonet lock.

According to one aspect of the disclosure, locking rivets are provided on the sterile container lid as a mating contour for the bayonet lock.

Thus, the cover performs the function of locking the overall system; in addition, when the cover is locked, the spring is pretensioned by the filter cassette between the cover and the sterile container lid. Only locking rivets in the sterile container lid serve as the mating contour for the bayonet lock and this is why the bayonet lock cannot be inserted incorrectly and locked in the wrong position. The spring forces absorbed by the cover are transmitted via the locking rivets into the cover structure. This simple and secure fastening of the cover and hence of the entire filter system to the sterile container lid ensures uncomplicated handling. In addition, the filter cassette can be checked on both sides quickly and easily by simply removing the cover.

The sterile container according to the disclosure, in particular for the receiving and sterile storage of surgical instruments or surgical material, comprises a receiving space formed by a container bottom and container walls and a sterile container lid according to the disclosure for closing the receiving space.

According to one aspect of the disclosure, the filter system can ensure a sterile flow path between the container exterior and the container interior.

The filter system provided in the sterile container lid and the resulting permanent flow path enable a sterile pressure equalization between the container exterior and the container interior without recontaminating the sterile material in the container. A sterile barrier or a sterile barrier system is thus formed.

According to one aspect of the disclosure, the filter system can additionally implement an (inlet) valve function so that a further flow path is opened when a critical pressure difference between the container exterior and the container interior is reached.

According to one aspect of the disclosure, the spring can transfer a preload force to the filter cassette so that the filter cassette is pressed against the sterile container wall section, and when the critical pressure difference is reached or exceeded, the force acting on the filter cassette from outside opposite the preload force of the spring becomes greater than the preload force of the spring, so that the filter cassette is forcefully released from the sterile container wall section against the preload force of the spring.

This inlet function for high pressure change rates allows vapor sterilization and protects the container from damage. Thus, when a critical pressure difference between the container exterior and the container interior is reached, the filter cassette together with the seal, which is pressed by the spring against the sterile container lid, is lifted from the sterile container lid and opens a further flow path. The pressure difference, which leads to an opening of the additional flow path, is designed to be so high that the valve function is only triggered at pressure change rates which occur during a sterilization process.

In addition, the use of a conical centering instead of a linear guide prevents the filter cassette from tilting and thus blocking the valve function. Furthermore, the plug seat is not self-locking and the filter cassette cannot be placed in the wrong position when the valve function is closed.

BRIEF DESCRIPTION OF THE DRAWING FIGURES

DETAILED DESCRIPTION

Figure 1:
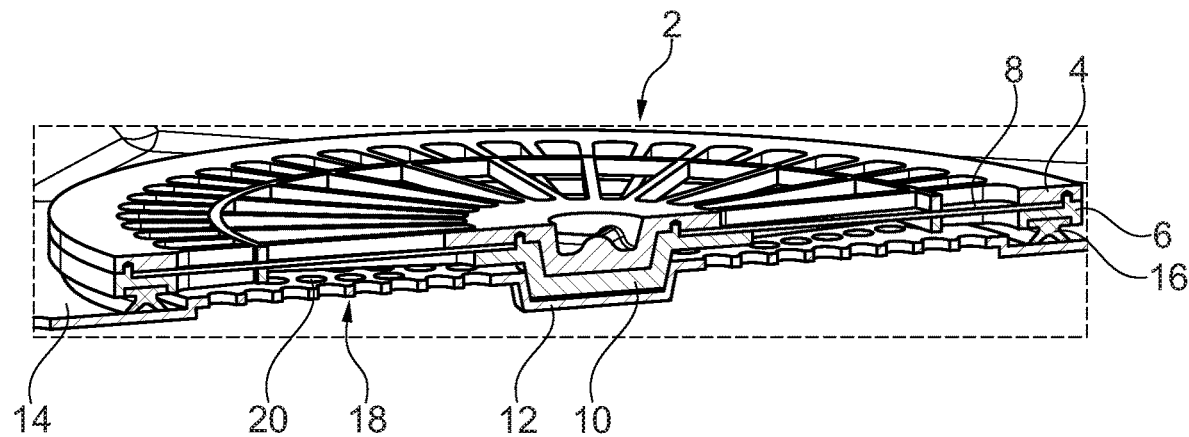
FIG. 1 is a cross-section view of the structure of a filter cassette and its positioning in a sterile container lid.
Figure 2:
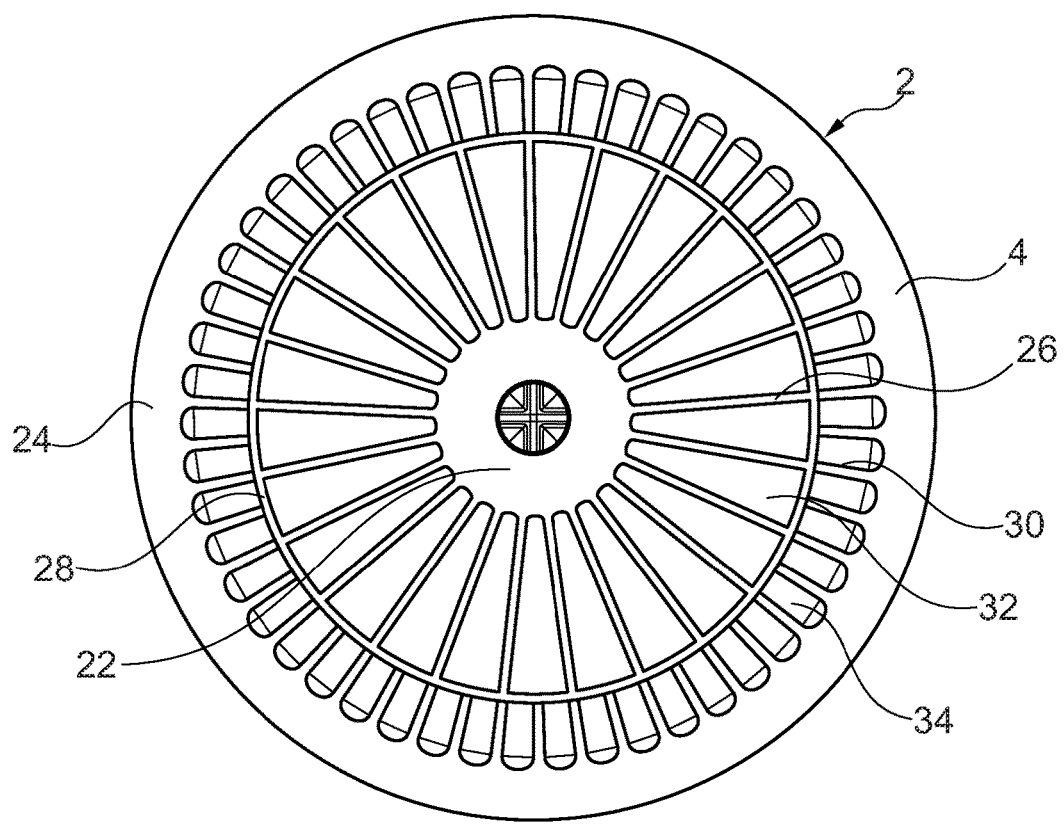
FIG. 2 shows a top view of the filter cassette.

With reference to FIGS. 1 and 2, a filter cassette 2 according to one embodiment is described below.

FIG. 1 shows the structure of a filter cassette 2 comprising an upper clamping disc 4 and a lower clamping disc 6. A disc-shaped filter element 8 is arranged between the upper clamping disc 4 and the lower clamping disc 6, more precisely clamped or pressed therebetween. A conical projection 10 is provided in the middle of the lower clamping disc 6, which is designed to be complementary to a conical seating 12—also in the middle or centrally arranged—in a sterile container lid 14, as one example of a sterile container wall section. The upper clamping disc 4 follows the contour of the lower clamping disc 6. A sealing ring 16 is provided on the outer edge of the lower clamping disc 6 on the side facing the sterile container lid 14. If the filter cassette 2 is inserted in the correct position in the sterile container lid 14, i.e. the lower clamping disc 6 faces the sterile container lid 14, the conical projection 10 slides into the conical seating 12 and the filter cassette 2 is aligned relative to the sterile container lid 14 or centered therein. Due to the conical seat between the filter cassette 2 and the sterile container lid 14, there is only one unique position in which the filter cassette 2 can be inserted, and the filter cassette 2 cannot get jammed when it is inserted or slipped in. The sealing ring 16 comes to rest on the sterile container lid 14 in such a way that a gas exchange opening 18 which has several circular openings 20 and is provided in the sterile container lid 14 is completely enclosed by the sealing ring 16 in the circumferential direction. The projection 10 and the seating 12 are each conical in shape. Basically, however, it is sufficient if only one of the two, i.e. the clamping disc 6 or the sterile container lid 14, is designed in a cone shape or has a centrally tapering sliding or contact surface, which positions the filter cassette 2 centrally to the gas exchange opening 18 when it is returned from a deflected position to its contact position.

FIG. 2 is a top view of the filter cassette 2 in which the design of the upper clamping disc 4 is shown. From an inner ring 22 to an outer ring 24, several first webs 26 extend evenly distributed in the circumferential direction. In addition, an intermediate ring 28 is formed between the inner ring 22 and the outer ring 24. From the intermediate ring 28 to the outer ring 24, several second webs 30 extend evenly between the first webs 26 distributed in the circumferential direction. This results in several first openings 32 between the inner ring 22 and the intermediate ring 28 and several second openings 34 between the intermediate ring 28 and the outer ring 24. The lower clamping disc 6 is designed according to the upper clamping disc. This design of the clamping discs 4 and 6 ensures that the first openings 32 and the second openings 34 form a relatively large area so that a gas flowing through the filter cassette 2 is impeded as little as possible by the clamping discs 4 and 6. In addition, the first and second webs 26 and 30 as well as the intermediate ring 28 provide a stable and rigid structure which absorbs and evenly distributes the forces acting on the filter cassette 2.

In the following, a filter system 36 according to one embodiment and its attachment to the sterile container lid 14 will be described with reference to FIGS. 3 and 4. Subsequently, the function of the filter system 36 provided in a sterile container will be explained.

Figure 3:
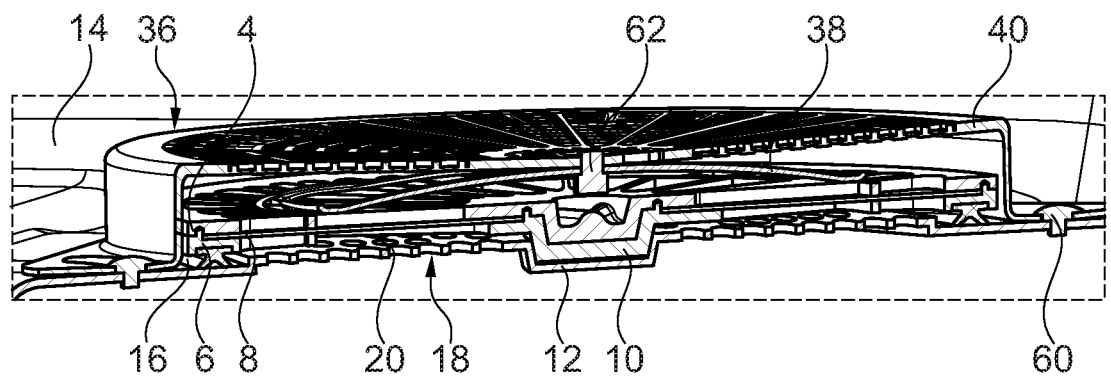
FIG. 3 is a cross-section view of the structure of a filter system and its fastening in a sterile container lid.
Figure 4:
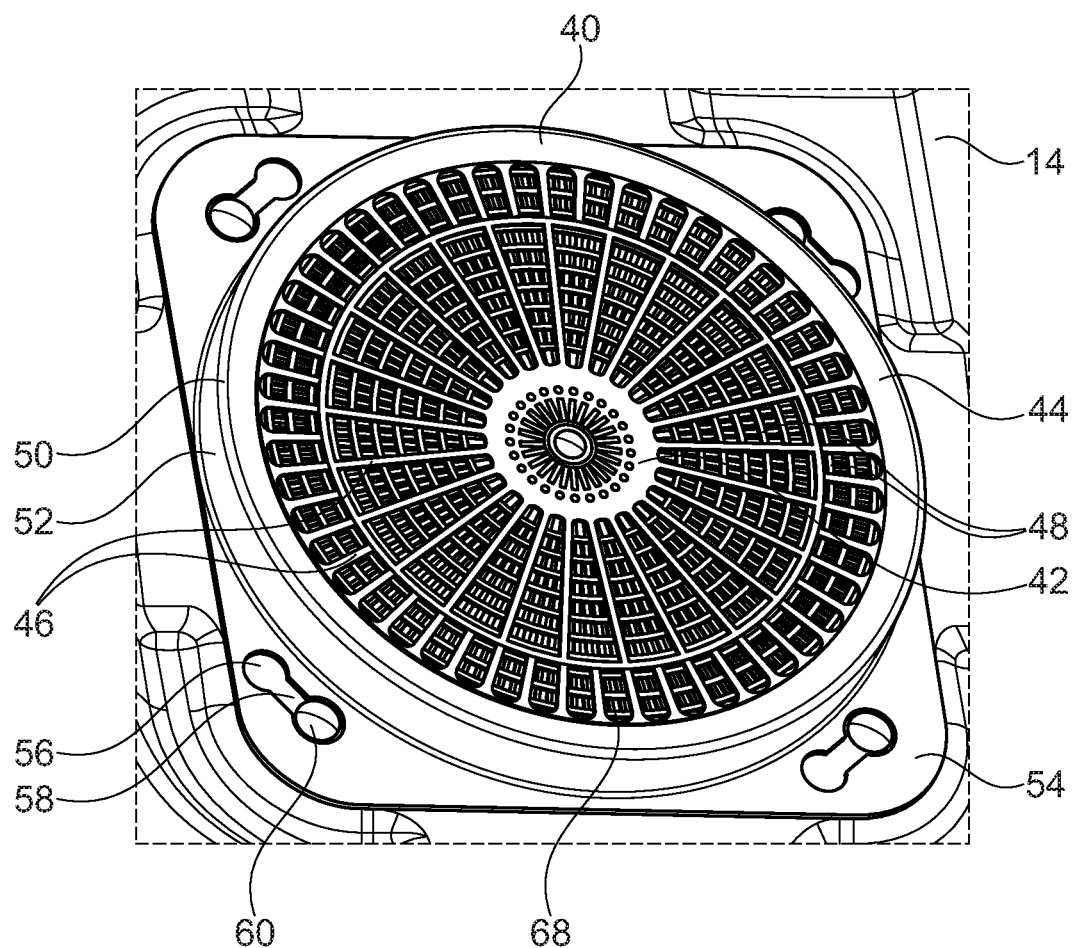
FIG. 4 shows a perspective view of a cover.

The filter system 36 shown in FIG. 3 consists of the filter cassette 2, a spring 38 and a cover 40. The filter cassette 2 is mounted in the cover 40 such that it can move axially against the preload force of the spring 38. The shape of the cover 40 is shown in FIG. 4. The cover 40 is similar to the upper clamping disc 4 shown in FIG. 2. Several cover webs 46 extend from a cover inner ring 42 to a cover outer ring 44. Several intermediate cover rings 48 are additionally formed between the cover inner ring 42 and the cover outer ring 44. On the outer edge 50 of the cover outer ring 44, there is a side wall 52. On the other end of the side wall 52 facing away from the outer edge 50, four flanges 54 are formed, so that the cover 40 has a square shape when viewed from above. Each flange has a locking opening 56 adjoined by a slot 58 which is smaller in width than the diameter of the locking opening 56. The locking openings 56 are dimensioned such that locking rivets 60 fastened to the sterile container lid 14 can be passed through the locking opening 56. A subsequent rotation of the cover 40 causes the locking rivets 60 to be pushed into the slots 58 and the cover 40 to be firmly connected to the sterile container lid 14.

Figure 5:
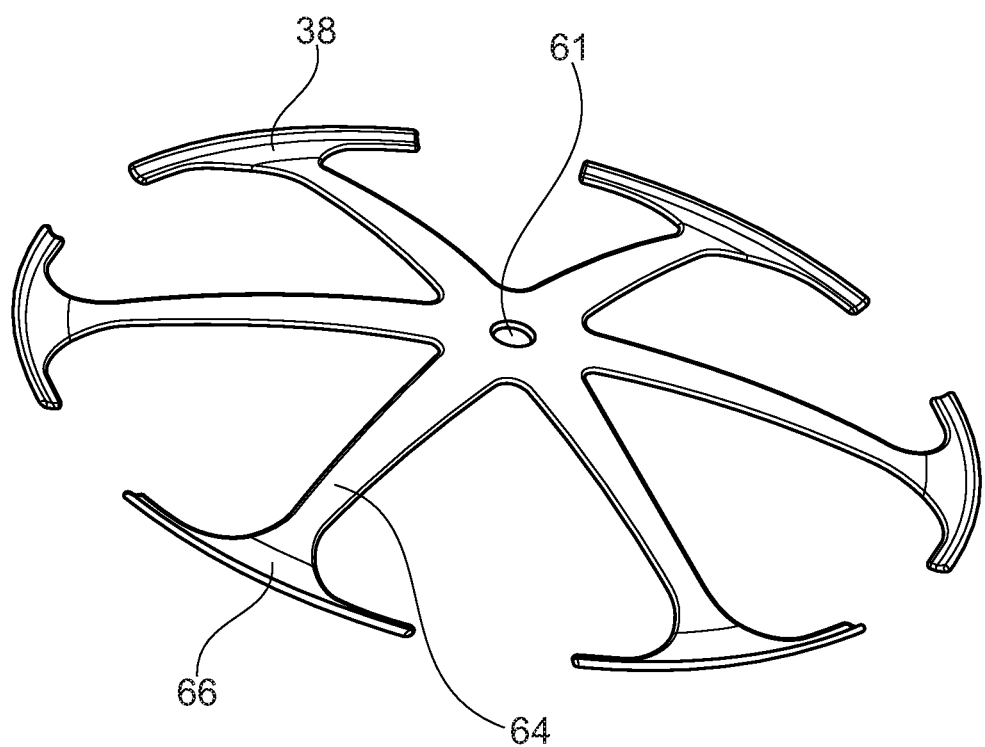
FIG. 5 shows a perspective view of a spring.

FIG. 5 shows the spring 38 which is formed in a spoke-like manner as a disc spring. Starting from a central fixing opening 61, into which a central pin 62 shown in FIG. 3 can be inserted for fixing the spring 38 to the cover 40, several spokes 64 having their radially outer ends realized in a T-shaped design extend in the radial direction outwards. In other words, the spokes 64 are widened circumferentially at their radially outer end 66. This makes it possible to transfer a contact pressure evenly in the circumferential direction.

In the filter system 36 shown in 3, the spring 38 is fastened by means of the pin 62 in the middle of cover 40 on the side of cover 40 facing the sterile container lid 14. The filter cassette 2 is positioned between the cover 40 with the spring 38 and the sterile container lid 14, so that the spring 38 is supported by the cover 40 and the filter cassette 2, more precisely the upper clamping disc 4. As the spring 38 is designed as a disc spring, the spring 38 is supported in the outer area of the filter cassette 2, which leads to the spring force being introduced into the filter cassette 2 near the sealing ring 16. As a result, the sealing ring 16 bears evenly and securely against the sterile container lid 14 in the circumferential direction and thus reliably produces a sealing. In other words, the uniform preload force of the spring 38 in the circumferential direction advantageously always ensures a uniform pressure force of the sealing ring 16 in the circumferential direction. The design of the upper clamping disc 4 and the lower clamping disc 6 is adapted in such a way that they are additionally reinforced in the area of force application and transmission, i.e. in the outer area, by the intermediate ring 28 and the second webs 30. Since the spring force is absorbed centrally in the cover 40 and transmitted by it via the locking rivets 60 into the sterile container lid 14, the cover 40 is reinforced along the entire radial extension between the cover inner ring 42 and the cover outer ring 46 with numerous cover webs 46 and cover intermediate rings 48. As a result, a large number of small cover openings 68 are also formed in the cover 40. These allow a gas exchange and additionally protect the filter cassette 2 from mechanical damage.

The filter system 36 described above is fixed in a sterile container lid 14 which in turn serves to close a (not shown) sterile container. The filter system 36 is installed in just two simple steps. First, the filter cassette 2 or the conical projection 10 of the lower clamping disc 6 is inserted into the sterile container lid 14 or the conical seating 12. Next, the locking openings 56 of the cover 40 are placed over the locking rivets 60 and the cover 40 is securely locked only by a small rotation, i.e. according to the principle of a bayonet lock. The filter cassette 2 is fixed in its position by the spring 38 fastened in the cover 40. This does not create a firm connection between the spring 38 and the filter cassette 2, which simplifies installation, n other words, the spring 38 and the filter cassette 2 slide off each other and the spring 38 is pretensioned by the cover 40 and the filter cassette 2 when the cover 40 is being locked. This fact is of particular advantage with regard to process reliability, since no component can be forgotten during assembly or reassembly. The reason for this is the haptic feedback that the user experiences when the system has been completely installed. Without the cover 40, the filter cassette 2 cannot be locked and without the filter cassette 2, the spring 38 is not pretensioned and the user does not receive any haptic feedback when locking the cover 40. In other words, an assembly error is detected if the cover 40 does not have to be pressed against the sterile container lid 14 against the preload force of the spring 38.

Furthermore, it should be mentioned that the filter cassette 2 can be replaced very easily or checked on both sides, since only the bayonet lock of the cover 40 needs to be opened and the cover removed by a slight rotation. Cleaning is also very easy. In addition, the entire filter system 36 is of very simple construction, as it essentially consists of only two parts, namely the filter cassette 2 and the cover 40 with the spring 38 fastened therein. This means that there are no small parts or individual components at any time, which simplifies handling. In addition, the small number of components and the lightweight design concepts used reduce the overall weight of the filter system. Especially due to the low movable inertial mass, sterility can be guaranteed with a high degree of certainty even during transport, despite the accelerations prevailing there.

In a normal operating condition of the sterile container, i.e. when a pressure difference between the container exterior and the container interior is less than a predetermined critical pressure difference, the spring 38 presses the filter cassette 2, in particular the sealing ring 16, against the sterile container lid 14. This creates a sterile flow path from the container exterior, through the gas exchange opening 18 in the sterile container lid 14, the filter cassette 2 and the cover 40, into the container interior, or vice versa. Due to the linear pressing action on the filter cassette 2 by the spring 38 designed as a disc spring and owing to the use of a conical seat, which does not require a continuous bore in the filter cassette for centering, only one seal is required to ensure a sterile barrier. In addition, a seal with a high compression height can be used to compensate for larger production tolerances.

However, if, e.g. in the case of a sterilization process, the pressure outside the container increases and thus the pressure difference between the container exterior and the container interior exceeds the predetermined critical pressure difference, the filter cassette 2 is pressed toward the cover 40 against the preload force of the spring 38. This causes the filter cassette 2 to lift off from the sterile container lid 14, and the sealing ring 16 no longer comes into contact with the sterile container lid 14 for a secure sealing or only to an insufficient extent. This creates a second, non-sterile flow path from the container exterior, through the gas exchange opening 18 in the sterile container lid 14, between the filter cassette 2 and the side wall 52 of the cover 40 and through the cover 40 into the container interior. This second flow path is necessary so that the pressure compensation can take place more quickly with a large pressure difference and the sterile container is thus protected from damage. The flow rate of the first, sterile flow path limited by the filter element 8 would not be sufficient for this.

As soon as the pressures inside and outside the container are equal again, i.e. when the pressure difference becomes smaller than the critical pressure difference, the spring 38 pushes the filter cassette 2 toward the sterile container lid 14. In this process, the conical projection 10 of the lower clamping disc 6 slides into the conical seating 12 of the sterile container lid 14. Consequently, the filter cassette 2 is guided safely when pushed back by the spring 38 and is automatically centered in the sterile container lid 14. Due to the conical shape or the resulting conical seat, the filter cassette 2 cannot get jammed and the valve function of the filter system 36 can be ensured, i.e. blocking of the valve function is excluded. The centering of the filter cassette 2 in the sterile container lid 14 is particularly important so that the sealing ring 16 securely surrounds the gas exchange opening 18 formed in the sterile container lid 14 and thus the gas exchange by the filter system 36 is only possible via the sterile flow path.

Apart from the embodiment described above, alternative designs of the filter cassette 2, filter system 36, sterile container lid 14 and sterile container are also possible. For example, a conical seating can be provided on the lower clamping disc 6, which is designed to be complementary to a conical projection provided on the sterile container lid 14. In addition, the spring 38, for example, can be fastened to the upper clamping disc 4 of the filter cassette 2 and be supported on the side of the cover 40 facing the filter cassette 2.

The invention claimed is:

1. A sterile container comprising:
a sterile container wall section having at least one gas exchange opening;
a gas-permeable filter cassette configured for insertion in or arrangement on the sterile container wall section;
a cover which is mountable on the sterile container wall section; and
a spring which is fastened to the cover, the spring being configured to exert a prestressing force in order to press the filter cassette onto the sterile container wall section, when the cover is mounted on the sterile container wall section,
the filter cassette comprising a filter element arranged in the filter cassette and a first conical centering portion configured for centering the filter cassette with respect to the sterile container wall section,
the sterile container wall section comprising a second centering portion,
the first conical centering portion of the filter cassette cooperable in a non-self locking manner with the second centering portion provided on the sterile container wall section for centering the filter cassette with respect to the sterile container wall section when the filter cassette is inserted in or arranged on the sterile container wall section.

2. The sterile container according to claim 1, wherein the first conical centering portion comprises one of a conical projection and a conical seating, and the second centering portion comprises the other of said conical projection and conical seating so that the first conical centering portion and the second centering portion form a non-self locking conical seat when the filter cassette is inserted in or arranged on the sterile container wall section.

3. The sterile container according to claim 1, wherein the filter cassette is formed from an upper clamping disc and a lower clamping disc.

4. The sterile container according to claim 3, wherein the filter element is arranged between the upper clamping disc and the lower clamping disc.

5. The sterile container according to claim 1 further comprising a sealing ring provided on the filter cassette.

6. The sterile container according to claim 5, wherein the sealing ring is provided on an outer peripheral region of the filter cassette and on a side of the filter cassette that faces the sterile container wall section when the filter cassette is inserted in or arranged on the sterile container wall section.

7. The sterile container according to claim 1, wherein, when the cover is mounted to the sterile container wall section, the filter cassette is received in the cover so as to be axially movable against the prestressing force of the spring.

8. The sterile container according to claim 1, wherein the spring is a leaf spring or a disc spring.

9. The sterile container according to claim 1, wherein the spring is fastened to the cover.

10. The sterile container according to claim 1, wherein the spring is fastened to the cover by a central pin.

11. The sterile container according to claim 1, wherein the spring is supported on the filter cassette.

12. The sterile container according to claim 1, wherein the spring is supported in the center of the cover.

13. The sterile container according to claim 1 further comprising a sterile container lid, wherein the sterile container lid comprises the filter cassette, cover and spring, and wherein the cover is lockable to the sterile container lid.

14. The sterile container according to claim 13 further comprising a bayonet lock, wherein the cover is lockable to the sterile container lid with the bayonet lock.

15. The sterile container according to claim 13 further comprising a container bottom and container walls, wherein the container bottom and container walls form a receiving space, and wherein the sterile container lid is configured for closing the receiving space.

16. The sterile container according to claim 1, wherein the filter cassette, cover and spring comprise a filter system, and wherein the filter system performs a valve function so that, when a critical pressure difference is reached between an exterior of the container and an interior of the container, a flow path is opened.

17. The sterile container according to claim 16, wherein the spring transfers a biasing force to the filter cassette so that the filter cassette is pressed against the sterile container wall section, and wherein, when the critical pressure difference is reached or exceeded, an outside force acts on the filter cassette in a direction opposite of the prestressing force of the spring, said outside force being greater than the prestressing force of the spring, so that the filter cassette is forcefully opened from the sterile container wall section against the prestressing force of the spring.

18. The sterile container according to claim 1, wherein the cover, the spring, the filter cassette and the sterile container wall section are arranged in this order from a sterile container inner side towards a sterile container outer side.

19. The sterile container according to claim 18, further comprising a sealing ring provided on the filter cassette, wherein the sealing ring is provided on an outer peripheral region of the filter cassette and on a side of the filter cassette that faces the sterile container wall section when the filter cassette is inserted in or arranged on the sterile container wall section, the sealing ring providing a seal between the filter cassette and the sterile container wall section and completely surrounding the gas exchange opening provided in the sterile container wall section, and wherein the spring presses the sealing ring onto the sterile container wall section.

20. The sterile container according to claim 18, wherein the filter cassette is formed from an upper clamping disc and a lower clamping disc, wherein a sealing ring is provided in an outer peripheral portion of the lower clamping disc and faces the sterile container wall section, the sealing ring providing a seal between the lower clamping disc and the sterile container wall section and completely surrounding the gas exchange opening provided in the sterile container wall section, and wherein the spring presses the sealing ring onto the sterile container wall section.

21. The sterile container according to claim 1, wherein the spring is a disc spring and is fastened to the cover by a central pin.

* * * * *